United States Patent [19]

Gedouin et al.

[11] Patent Number: 5,612,038
[45] Date of Patent: Mar. 18, 1997

[54] PRODUCT WITH LIPOLYTIC ACTIVITY AND ITS METHOD OF PREPARATION

[75] Inventors: Jean Gedouin; Romuald Vallee, both of Saint Malo, France

[73] Assignee: Codif Inernational SA, France

[21] Appl. No.: 365,567

[22] Filed: Dec. 28, 1994

[30] Foreign Application Priority Data

Jan. 18, 1994 [FR] France .................... 94 00686

[51] Int. Cl.⁶ .................................... A61K 35/78
[52] U.S. Cl. ........................................ 424/195.1
[58] Field of Search ........................... 424/195.1

[56] References Cited

FOREIGN PATENT DOCUMENTS

| 0438302 | 1/1991 | European Pat. Off. . |
|---|---|---|
| 2438481 | 5/1980 | France . |
| 2581876 | 11/1986 | France . |
| 2666965 | 3/1992 | France . |
| 5145 | of 1914 | United Kingdom . |

OTHER PUBLICATIONS

Chem. Abst. 121(18): 212608w & 213021m, 1994.

Primary Examiner—John W. Rollins
Attorney, Agent, or Firm—Laff, Whitesel, Conte & Saret, Ltd.

[57] ABSTRACT

Product with lipolytic activity and its method preparation.

The present invention relates to a process for preparing a sea-weed based product with lipolytic activity. Said process consists of subjecting sea-weed to the following stages:

a) rehydration of previously lyophilized sea-weed to the original level of humidity with demineralized water, b) lixiviation in semi-fluid bed of the rehydrated sea-weed, c) elimination from the extraction juice of the macromolecules and particles which are greater in size than 0.22 micron, d) concentration of the organic elements by eliminating the minerals.

11 Claims, No Drawings

PRODUCT WITH LIPOLYTIC ACTIVITY AND ITS METHOD OF PREPARATION

The present invention relates to a product with lipolytic activity and its method of preparation. It also concerns pharmaceutical or cosmetic compositions containing said product as active principle.

In the prior art, the lipolytics used have been the same for many years, i.e. xanthic bases such as caffeine and theophylline, L-carnithine and the silanols.

These molecules, although effective, are manufactured by chemical synthesis or by extraction from natural products. In both cases, the preparation of the active principles involves numerous chemical reagents. This gives rise to cosmetics containing these active principles having a negative image with the consumers.

The object of the invention is to propose a new product with lipolytic activity extracted from natural products without involving chemical reagents.

This invention is based on the unexpected discovery that sea-weed extracts have a direct lipolytic activity on cells and more particularly on adipocytes.

Until now, this activity has never been demonstrated as far as sea-weed is concerned.

The first stages for the preparation of the sea-weed extracts are carried out in accordance with a process already described in French patent application No. 92 09497 filed in the name of the present applicant.

Said process consists of:

a) subjecting previously lyophilized sea-weed to rehydration with demineralized water to the original level of humidity, b) subjecting the rehydrated sea-weed to a lixiviation in semi-fluid bed with demineralized water, c) eliminating the macromolecules and particles larger than 0.22 micron from the extraction juice.

The characteristics of the process and the apparatus used are described in greater detail in patent application No. 92 09497.

In order to obtain a product with lipolytic activity, a new stage has been added to the process. This stage consists of concentrating the organic elements by eliminating the minerals.

A) EXAMPLES OF PREPARATION OF SEA-WEED EXTRACT ACCORDING TO THE PRESENT INVENTION

Example 1

1.2 Kg of sea-weed of the type *Laminaria digitata*, cut into roughly 1 cm pieces, was lyophilized then rehydrated with demineralized water.

After rehydration for 15 minutes in 6.8 litres of water, these pieces of sea-weed were subjected to a lixiviation in semi-fluid bed. The maximum yield from the extraction process is achieved at the end of approximately one hour and a half of lixiviation in semi-fluid bed.

The extraction juice thus obtained was then subjected to a purifying process. For this purpose, said extraction juice was passed through a first filter with retention threshold of approximately 128 microns. The function of this filter is to eliminate the sea-weed debris.

The filtrate is then passed through two filters of the frontal type with cellulose membrane. The retention thresholds of these two filters are 10 and 1 microns respectively.

The filtrate obtained is then purified by tangential microfiltration through a filter with retention threshold of 0.22 micron. The objective of this operation is to eliminate from the filtrate macromolecules such as polysaccharides and microorganisms.

The filtrate obtained is a clear liquid, pale yellow in colour, containing small molecules such as trace elements, amino acids, peptides, proteins, etc.

The preceding stages as well as the analytical characteristics of the extract are described in greater detail in patent application No. 92 09497.

The filtrate resulting from the preceding stage is then concentrated to a voluminal concentration factor VCF 35 by nanofiltration. This stage is carried out on a system using a piston pump allowing the filtrate to be passed through a membrane with retention threshold of 400 Daltons. The pressure of the pump during the course of the concentration is between 20 and 40 bars. In such a system, the monovalent minerals and some of the bivalent minerals pass through the filter and are eliminated. At the same time the retentate circulating in a closed circuit passes through the filter several times. The result is a progressive concentrating of the organic component of the retentate as the minerals are eliminated. The retentate obtained is called extract 1.

Extract 1 has the following analytical characteristics:

| | |
|---|---|
| Proteins | 11% |
| Lipids | negligible |
| Minerals | 20% |
| Glucides | 69% |
| ORGANOLEPTIC INVESTIGATION | |
| Appearance | slightly cloudy liquid |
| Colour | dark brown |
| Odour | characteristic |
| PHYSICOCHEMICAL TESTS | |
| pH at 20° C. | 4.88 |
| Density at 20° C. | 1.061 |
| Refractive index at 20° C. | 13.5% |
| Electrical conductance | 18.6 mS |
| Dry materials (2 gr at 105° C. for 2 hours) | 12.07% |
| Mineral matter (at 550° C.) | 2.40% |
| MINERAL ANALYSIS | |
| Total nitrogen | 2.175 g/l |
| Magnesium | 3.27 g/l |
| Chlorides | 6.4 g/l |
| Calcium | 1.3 g/l |
| Potassium | 3.6 g/l |
| Sulphates | 4.8 g/l |
| Phosphorus | 0.48 g/l |
| Total iron | 3.9 mg/l |
| zinc | 80 mg/l |
| Copper | 0.76 mg/l |
| Manganese | 10 mg/l |

INVESTIGATION OF AMINO ACIDS

An analysis by thin-layer chromatography after hydrolysis of the extract reveals the presence of the following amino acids: alanine, glutamic acid, valine, phenylalanine, leucine, isoleucine or methionine.

Example 2

The same operations are carried out as in example 1 to obtain extract 1 which is then allowed to settle for 24 hours and which is filtered to eliminate the insoluble elements. The filtrate obtained is called extract 2.

Example 3

The same operations are carried out as in example 1 but the nanofiltration is continued so as to concentrate the extract to a voluminal concentration factor VCF 90.

A tangential ultrafiltration at 1000 Daltons is then carried out on the retentate in order to eliminate all molecules having a molecular weight greater than 3000–4000 Daltons. These molecules, by reason of their size, are incapable of crossing the cutaneous barrier.

The filtrate obtained is called extract 3.

Example 4

Extract 4 is obtained by lyophilization of extract 3.

B) DETERMINATION OF THE LIPOLYTIC ACTIVITY OF THE SEA-WEED EXTRACTS ACCORDING TO THE INVENTION

The lipolytic activity of each prepared extract was measured using adipocytes isolated from rats.

In the course of lipolysis, the intracellular triglycerides will be hydrolyzed as glycerol and fatty acids liberated into the extracellular medium. In order to determine the lipolytic activity of each sea-weed extract according to the invention, the quantities are determined of the fatty acids and the glycerol liberated by the adipocytes into the incubating medium in the presence of the sea-weed extracts. These values are then compared with those which are obtained in the absence of sea-weed extracts.

The determination of the quantities of fatty acids and glycerol is carried out with the aid of commercialized quantity-determination kits (Biolyon$^{(R)}$ kit for the fatty acids and Boehringer$^{(R)}$ kit for the glycerol).

Isolation of the rat adipocytes

The rat used is a male Sprague Dawley rat weighing 400 g. The adipocytes of the epididymal tissue were separated by means of collagenase 0.1% in a separating medium made up of MEM medium without phenol red with the addition of 50 IU/ml penicillin, 50 µg/ml streptomycine, 0.13% sodium bicarbonate and 0.5% glutamine.

The cellular suspension was filtered then washed in the incubating medium made up of the separating medium with the addition of 0.5% delipidated BSA.

The cellular viability was checked by oxymetry; the oxygen consumption of the adipocytes was within the range of values usually obtained in the laboratory.

Incubation protocol

The extracts to be tested were directly diluted in the incubating medium. They were put in contact with the appropriate number of cells for two hours at 37° C. Incubations of "reference solutions without product" or "reference solution without cells" were carried out at the same time. Each experimental condition was carried out in triplicate.

Expression of the results

The results obtained were entered in tables 1, 2, 3 and 4.

The values were expressed as micromoles of fatty acids (or glycerol) formed during an incubation period of 0.5, 2 and 4 hours and for a given number of cells. The averages were obtained from the triplicates, then the average values found in the incubations carried out in the presence of the products being studied and in the absence of the cells were subtracted.

Tables 1, 2, 3, and 4 show the lipolytic activity of the extracts 1 to 4.

The lipolytic activity increases overall with time with a maximum at the end of 2 hours, which demonstrates that there is assimilation of the active principle of the extracts into the adipocytes.

It will be noted that the stimulation factor for hydrolysis of the triglycerides as non-esterified fatty acids is in the order of 140% compared with the reference solutions in the absence of sea-weed extracts.

It will also be noted that there are no significant differences in lipolytic activity between the extracts 1, 2, 3 and 4. This tends to show that the stages added after the nanofiltration at 400 Daltons do not significantly improve the effectiveness of the extract.

The quantity-determination of the glycerol, although less precise than the quantity-determination of the fatty acids, confirms the stimulation of lipolysis in the presence of the sea-weed extracts according to the invention.

Having been subjected to a tangential ultrafiltration of 1000 Daltons, extract 3 no longer contains molecules having a molecular weight greater than 3000–4000 Daltons. However it has a lipolytic activity. The active principles therefore have a molecular weight less than 3000–4000 Daltons and they will be capable of crossing the cutaneous barrier of which the crossing threshold is approximately 6000 Daltons.

C) COMPARISON OF THE LIPOLYTIC ACTIVITY OF THE SEA-WEED EXTRACTS WITH KNOWN LIPOLYTICS

Table 5 compares the lipolytic activity of the sea-weed extract 1 with several reference molecules belonging to the family of known lipolytics. The concentrations of the reference solutions were chosen so as to present a maximum of activity but without presenting a cytotoxicity in respect of the adipocytes. The destruction of the cells would indeed lead to a release of fatty acid and glycerol into the incubating medium which would falsify the determination of the lipolytic activity of the reference solutions.

TABLE 5

| PRODUCTS | CON-CENTRATIONS | Eq DRY EXTRACT | LIPOLYTIC ACTIVITY |
| --- | --- | --- | --- |
| L. Carnithine | 0.1 mM | 0.01% | 120 |
| Caffeine | 0.1 mM | 0.02% | 152 |
| Theophylline | 0.1 mM | 0.02% | 132 |
| Mannuronate of methyl silane-triol | 1.0% | 0.01% | 140 |
| Extract 1 | 0.1% | 0.01% | 145 |

It follows from the analysis of table 5 that the extract 1 resulting from the process described in example 1 has an activity equal to the lipolytics ordinarily used in cosmetics and this for percentages of active molecules of the same order of magnitude.

The sea-weed extracts according to the present invention do not present any cytotoxicity for extracts 1 to 3 up to a concentration of 1% and for extract 4 (lyophilized product) up to a concentration of 0.1%. A slight toxicity towards the adipocytes is noted as from a concentration of 10% and respectively 1% for the lyophilized product.

Thus it is shown that the results concerning the hydrolysis of triglycerides are due to an activity at the level of the adipocytes and not to a destruction of these.

It will be noted that the lipolytic products according to the invention have the advantage when compared with existing lipolytics that they are extracted from natural products by a process which does not involve any chemical reagent. The result is the perfecting of new cosmetic compositions which meet the real needs of the consumers.

A study relating to the stability over a period of time of the sea-weed extracts according to the invention has also been carried out. The results are shown in table 6. It will be noted on studying said table that the lipolytic activity of extract 1 measured at a 6-month interval has not undergone any appreciable variations.

TABLE 6

STABILITY OF THE LIPOLYTIC ACTIVITY over a period of time

| T = 2 h | CONCENTRATION (%, V/V) | | | | |
|---|---|---|---|---|---|
| | 0 | 0.05 | 0.1 | 0.5 | 1 |
| Extract 1 | 13 +/– 0 | 14 +/– 1 | 15 +/– 1 | 16 +/– 1 | 14 +/– 1 |
| % | 100 | 107 | 122 | 129 | 107 |
| Extract 1 6 months later | 15.03 +/– 1.44 | | 21.73 +/– 0.85 | | 17.27 +/– 0.98 |
| % | 100 | | 145 | | 115 |

Thanks to the sea-weed extracts according to the invention, pharmaceutical or cosmetic compositions are obtained which have a lipolytic activity. The application of these compositions on to the skin results in a local slimming. Such compositions may especially be used in the treatment of cellulite.

The following examples are given by way of illustrating compositions according to the invention. The proportions of the constituents are expressed in percentage by weight.

| Example 1: slimming gel | | |
|---|---|---|
| Water | | 88.00 |
| Propylene glycol | | 1.00 |
| Cyclomethicone | | 1.00 |
| Vaseline oil | | 5.00 |
| Sea-weed extract 1 | | 1.00 |
| Sepigel 305 | | 3.00 |
| Preservative, perfume | q.s. (sufficent quantity) | 100 |
| Example 2: slimming lotion to be atomized | | |
| Water | | 85.00 |
| Propylene glycol | | 2.00 |
| Cetiol ME | | 1.00 |
| Rosewater | | 10.00 |
| Sea-weed extract 1 | | 1.00 |
| Preservative, colour, perfume | q.s. | 100 |
| Example 3: slimming, draining cream | | |
| Vaseline oil | | 5.00 |
| Stearic acid | | 1.00 |
| Cetyl alcohol | | 1.50 |
| Sweet-almond oil | | 4.00 |
| Triethanolamine | | 1.20 |
| Propylene glycol | | 1.00 |
| Water | | 81.00 |
| Carbomer 940 | | 0.50 |
| Plant extracts | | 3.00 |
| Sea-weed extract 1 | | 1.00 |
| Perfume, colour | q.s. | 100 |

(Please see in conjunction with original tables)

Table 1: QUANTITY-DETERMINATION OF NON-ESTERIFIED FATTY ACIDS AS μM OF FATTY ACIDS RELEASED (after 0.5 hour incubation)

Table 2: QUANTITY-DETERMINATION OF NON-ESTERIFIED FATTY ACIDS AS μM OF FATTY ACIDS RELEASED (after 2 hours' incubation)

Table 3: QUANTITY-DETERMINATION OF NON-ESTERIFIED FATTY ACIDS AS μM OF FATTY ACIDS RELEASED (after 4 hours' incubation)

Table 4: QUANTITY-DETERMINATION OF NON-ESTERIFIED GLYCEROL AS μM OF GLYCEROL RELEASED (after 4 hours' incubation)

We claim:

1. A process for preparing a product with lipolytic activity, wherein a dehydrated sea-weed of the type Laminaria is subjected to the following steps:

a) rehydrating a previously dehydrated lyophilized sea-weed to its original level of humidity, said rehydration being carried out with demineralized water, b) lixiviating said rehydrated sea-weed in semi-fluid bed, c) filtering to eliminate macromolecules and particles having a size larger than 0.22 microns from an extraction juice obtained by said lixiviation of step b), and d) concentrating organic elements by eliminating minerals from the extraction juice filtered in step c.

2. A process for preparing a product with lipolytic activity, wherein said process comprises subjecting *Laminaria digitata* sea-weed having a direct lipolytic activity to the following steps:

a) rehydrating a previously lyophilized sea-weed to an original level of humidity with demineralized water, b) lixiviating in a semi-fluid bed of the rehydrated sea-weed, c) filtering macromolecules and particles larger in size than 0.22 micron from an extraction juice obtained by said lixiviation of step b), and d) concentrating resulting organic elements by eliminating minerals therefrom.

3. The process according to claim 1 or claim 2, wherein the elimination of the minerals responsive to the filtering of step d) is carried out by nanofiltration.

4. The process according to claim 3, wherein the nanofiltration is carried out by using a filter with a retention threshold of 400 Daltons.

5. The process according to claim 4 wherein the elimination of the macromolecules and particles which are larger in size than 0.22 micron is carried out by tangential microfiltration using a filter with a retention threshold of 0.22 micron.

6. The process according to claim 3 wherein the elimination of the macromolecules and particles which are larger in size than 0.22 micron is carried out by tangential microfiltration using a filter with a retention threshold of 0.22 micron.

7. The process according to claim 1 or 2 wherein the elimination of the macromolecules and particles which are larger in size than 0.22 micron is carried out by tangential micro filtration using a filter with a retention threshold of 0.22 micron.

8. The process according to claim 7, wherein the tangential microfiltration is preceded by a frontal type of filtration by using a filter with a retention threshold of 1 micron.

9. The process according to claim 8, wherein the frontal type of filtration is preceded by a filtration of the same frontal type before using a filter with a retention threshold of 10 microns.

10. A product with lipolytic activity made by the process according to one of the claims 1 or 2.

11. A pharmaceutical or cosmetic composition, comprising a product according to claim 10 in an aqueous medium.

* * * * *